United States Patent
Grubb et al.

(10) Patent No.: US 8,268,576 B2
(45) Date of Patent: Sep. 18, 2012

(54) DIAGNOSIS OF AUTISM

(75) Inventors: Anders Grubb, Lund (SE); Naghi Momeni, Kalmar (SE)

(73) Assignee: Autism Biodiagnostic Ltd (GB)

( * ) Notice: Subject to any disclaimer, the term of this patent is extended or adjusted under 35 U.S.C. 154(b) by 0 days.

(21) Appl. No.: 13/166,143

(22) Filed: Jun. 22, 2011
(Under 37 CFR 1.47)

(65) Prior Publication Data
US 2012/0149038 A1 Jun. 14, 2012

Related U.S. Application Data

(63) Continuation of application No. 10/548,100, filed as application No. PCT/SE2004/000193 on Mar. 2, 2004, now abandoned.

(30) Foreign Application Priority Data

Mar. 4, 2003 (SE) .................................... 03005865

(51) Int. Cl.
*G01N 33/53* (2006.01)
*G01N 33/542* (2006.01)
*A61K 38/00* (2006.01)

(52) U.S. Cl. ......... 435/7.92; 435/7.9; 435/7.1; 530/300; 530/326

(58) Field of Classification Search .................... None
See application file for complete search history.

(56) References Cited

U.S. PATENT DOCUMENTS 6,998,243 B2 2/2006 Jackowski
2002/0006640 A1 1/2002 Ni

FOREIGN PATENT DOCUMENTS

EP 0969015 1/2000
EP 0979828 2/2000

OTHER PUBLICATIONS

Biological Psychiatry, vol. 50, 2001 Lee Ann Green et al, "Oxytocin and Autistic Disorder: Alterations in Peptide Forms" pp. 609-613, p. 610, col. 2; p. 609, col. 1.

*Primary Examiner* — Olga N Chernyshev
(74) *Attorney, Agent, or Firm* — Popovich, Wiles & O'Connell, P.A.

(57) ABSTRACT

A method for diagnosing autism in a subject is performed by determining the presence and concentration of specific peptides in the body fluid. The peptides have the amino acid sequences SKITHRIHWESASLL (SEQ ID NO: 1), SSKITHRIHWESASLL (SEQ ID NO: 2), and SSKITHRIHWESASLLR (SEQ ID NO: 3) with the molecular masses 1779 +/−1 Da, 1865 +/−1 Da and 2022 +/−1 Da, respectively.

3 Claims, 1 Drawing Sheet

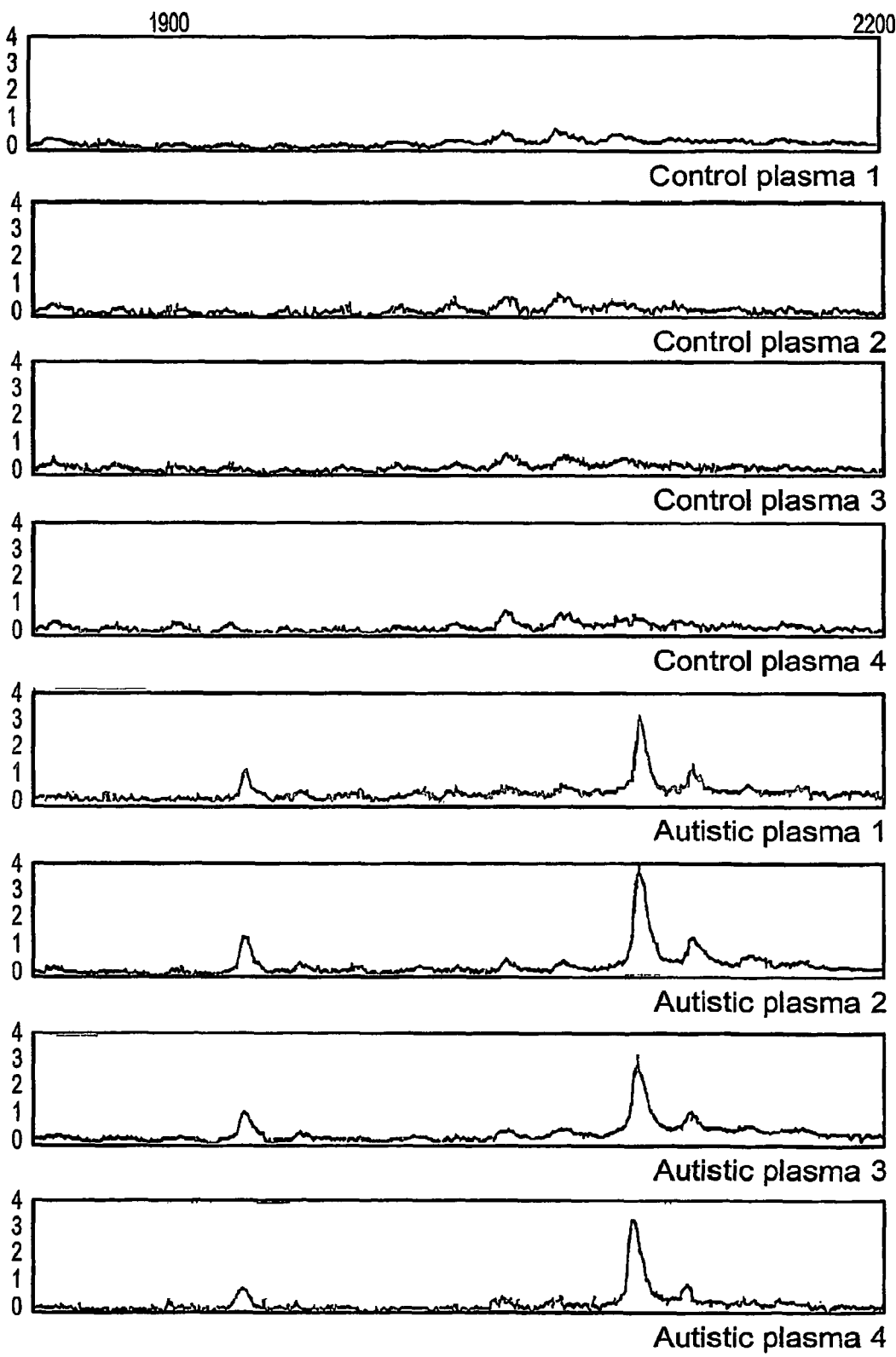

SEQUENCE LISTING

```
<160> NUMBER OF SEQ ID NOS: 3

<210> SEQ ID NO 1
<211> LENGTH: 15
<212> TYPE: PRT
<213> ORGANISM: Homo sapiens

<400> SEQUENCE: 1

Ser Lys Ile Thr His Arg Ile His Trp Glu Ser Ala Ser Leu Leu
1               5                   10                  15

<210> SEQ ID NO 2
<211> LENGTH: 16
<212> TYPE: PRT
<213> ORGANISM: Homo sapiens

<400> SEQUENCE: 2

Ser Ser Lys Ile Thr His Arg Ile His Trp Glu Ser Ala Ser Leu Leu
1               5                   10                  15

<210> SEQ ID NO 3
<211> LENGTH: 17
<212> TYPE: PRT
<213> ORGANISM: Homo sapiens

<400> SEQUENCE: 3

Ser Ser Lys Ile Thr His Arg Ile His Trp Glu Ser Ala Ser Leu Leu
1               5                   10                  15

Arg
```

DIAGNOSIS OF AUTISM

TECHNICAL FIELD

The present Invention relates to a method for diagnosis of autism by means of a simple test on a sample of a subject.

BACKGROUND OF THE INVENTION

Autism is the term for a symptom-complex of a subject meaning such a bad communication possibility with people around that the subject in question has to be taken care of by the society in different ways during its whole lifetime.

One to five out of 1000 persons born in Sweden suffer from autism. The diagnosis is difficult to establish and can take several years to secure. The pedagogical and social measures, which the society and the family of the autistic person have to take, are lifelong and extremely costly. The suffering of the ones affected and their families is great. No biochemical treatment is known (e.g., use of pharmaceuticals) so far.

The pathophysiology of autism involves abnormal communication between neurons, possibly associated with abnormal patterns peptides, e.g., neuropeptides in the brain. Abnormal levels of peptides might be revealed by proteomic studies of proteins/peptides below 10 kDa in spinal fluid and/or blood plasma. Detection of abnormal levels of peptides in autism will allow generation of new hypotheses concerning its pathophysiology and might facilitate diagnostics and suggest new treatment possibilities. Since most peptides are generated by proteolysis of larger precursor molecules abnormal levels of peptides might be caused by abnormal proteolytic activity.

There is very little biochemical research done and available concerning autism as there are no animal models available and there is a practical problem collecting a more substantive patient material.

In the prior art EP-A-0 979 828 discloses a method for diagnosing autism by determining specific peptides present in a biological fluid. The peptides which comprises 3 to 4 amino acids are said to indicate autism when present in high amounts.

EP-A-0 969 015 relates to a method for diagnosing a disease, such as autism, by identifying peptides present in a tissue of body liquid. The peptides are disclosed as having a length of 3 to 8 amino acids, and having a molecular weight of <1081.

Green, L. A. et al in Biological Psychiatry, 50: 609-613 (2001) discloses that the oxytocin concentration in plasma of autistic persons is different from the one in healthy persons. The amount of oxytocin-extened (OT-X) is higher in autistic patients, while the amount of oxytocin (9 amino acids) is lower.

US-A-2002/0006640 relates polypeptides and methods for diagnosis of inter alia autism.

None of these documents discloses the peptides of the present invention.

SUMMARY OF THE PRESENT INVENTION

The present invention is based on a hypothesis that the basis of autism is the presence of an abnormal peptide pattern in the brain and/or the fluids penetrating or surrounding the brain, i.e., blood and cerebrospinal fluid, and that some of these peptides might disturb the signals (e.g., carried neuropeptides), used by the brain for communication.

The invention is characterized in the determination of the presence or absence of certain proteins/peptides with specific amino acids sequences, present in a body sample, which proteins/peptides have the molecular masses of 1779+/−1 Da, 1865+/−1 Da and 2022+/−1 Da, respectively.

In particular the present invention relates to determining in a tissue sample, body liquid and/or plasma sample a higher than normal level of one or more of the following peptides

```
                                        (SEQ ID NO: 1)
         SKITHRIHWESASLL (SEQ ID NO: 2)
         SSKITHRIHWESASLL (SEQ ID NO 3)
         SSKITHRIHWESASLLR
```

In a preferred embodiment of the method, the amount of the peptide(s) is more than 10 times that present in a sample of a healthy subject.

In a further preferred embodiment, the respective peptide is determined using ELISA technology.

In another preferred embodiment, the respective peptide is determined using RIA technology.

In a further other preferred embodiment, the respective peptide is determined using a SELDI-TOF-MS system.

In a further aspect of the invention it relates to a kit for determining said peptides, whereby the kit comprises a marker for certain peptides having the molecular weights 1779, 1865 and 2022, respectively.

In a preferred embodiment thereof, it comprises a marker for one or more of the peptides encoded for by the amino acid sequence SSKITHRIHWESASLLR (SEQ ID NO: 3), SSKITHRIHWESASLL (SEQ ID NO: 2), and/or SKITHRIHWESASLL (SEQ ID NO: 1).

Body liquid means herein any body liquid such as blood, blood serum, blood plasma, spinal fluid, cerebrospinal fluid, and lymph.

The present peptides, specifically identified above, may be a fragment of a plasma protein called complementary factor C3.

DETAILED DESCRIPTION OF THE PRESENT INVENTION

The present invention has been confirmed in a pilot study using a so-called SELDI-TOF-MS (Ciphergen Biosystems Inc. Palo Alto, Calif. USA) technology, a new proteomics technology, whereby the peptide patterns of blood plasma of four autistic children and four non-autistic children were analysed and compared. Thereby it was found that at least three peptides, each containing 15 to 20 amino acids, were over represented in all autistic children in the molecular band 1700 to 2200 Dalton. Thereby the amount of said peptides were at least 10 times higher in the blood plasma of the autistic children compared to non-autistic children.

FIG. 1 shows eight different mass spectrometry profiles in the 1700 to 2200 Dalton band obtained from eight individuals, four without a diagnosis of autism and four diagnosed as autistic children. The upper four are mass spectrometry bands from the individuals without a diagnosis of autism, and the lower four are from the autistic children.

It is apparent that there are at least three different peaks appearing in the samples of the autistic children that differ considerably from those of children without a diagnosis of autism. When using appropriate molecular mass markers it is determined that at about 1779, 1865 and 2022 Daltons there are significant peaks present. The different peak areas represent amounts of the respective peptide present which amounts are more than ten times higher in samples from autistic children than in samples from children without a diagnosis of autism.

The structures of the peptides were determined using MS/MS mass spectrometry, whereby their amino acid sequences were determined to be SSKITHRIHWESASLLR (SEQ ID NO: 3), SSKITHRIHWESASLL (SEQ ID NO:2), and SKITHRIHWESASLL (SEQ ID NO: 1), respectively. The first peptide is known as complement C3f (NCBI accession number 1413205A), the second one lacks C-terminal arginine, and the third one further lacks N-terminal serine.

The concentrations of the selected peptides in e.g., plasma or spinal fluid samples can easily be determined by means of immunochemical techniques, such as ELISA or RIA. Antibodies will be used and labelling of antibodies and/or the antigen peptides will be performed according to general protocols using e.g., the chloramine T method for radiolabelling.

It is apparent that high levels in body fluids/tissue of these peptides identified above are at least markers of an autistic condition and can readily be used to diagnose autism. However, the determination of the presence of these peptides in high levels also means that a possible pathogenic mechanism of autism has been discovered and that this might lead to new possibilities of treatment of autism, e.g., by suppressing the formation of these peptides.

```
                                    (SEQ ID NO: 1)
SKITHRIHWESASLL, (SEQ ID NO: 2)
SSKITHRIHWESASLL,
and (SEQ ID NO: 3)
SSKITHRIHWESASLLR;
``` comparing the detected concentration of said one or more peptides with the concentration of said peptides in individuals not afflicted with autism; and diagnosing autism in said subject when at least one of said detected concentrations is more than ten times greater than the concentration of said peptides in individuals not afflicted with autism.

2. The method of claim 1, wherein the blood sample is plasma.

3. The method of claim 1, comprising:

analyzing a blood sample to detect the concentrations of all three of said peptides; and comparing the detected concentrations of said three peptides with the concentration of said three peptides in individuals not afflicted with autism; and

---

---

The invention claimed is:

1. A method for diagnosing autism in a subject suspected of suffering from autism, comprising:

analyzing a blood sample to detect the concentration of one or more peptides consisting of the following amino acid sequences:

diagnosing autism in said subject when all three of said detected concentrations are more than ten times greater than the concentrations of said three peptides in individuals not afflicted with autism.

* * * * *